United States Patent [19]

Krieger, Jr.

[11] Patent Number: 5,316,589
[45] Date of Patent: May 31, 1994

[54] METHOD FOR CONTROLLING STREET SURFACE POLLUTANTS

[76] Inventor: Frederick W. Krieger, Jr., 2510 Woolsey, Berkeley, Calif. 94705

[21] Appl. No.: 903,788
[22] Filed: Jun. 24, 1992
[51] Int. Cl.$^5$ .............................................. B08B 3/00
[52] U.S. Cl. .................................. 134/10; 134/22.11; 134/24; 134/42; 210/919; 210/920
[58] Field of Search ............... 134/10, 22.11, 22.12, 134/24, 34, 42; 137/236.1; 210/600, 749, 919, 920

[56] References Cited

U.S. PATENT DOCUMENTS

| | | | |
|---|---|---|---|
| 3,674,687 | 7/1972 | Quase | 137/236.1 |
| 3,874,926 | 4/1975 | Horne et al. | 134/22.12 |
| 4,025,360 | 5/1977 | Horne et al. | 134/24 |
| 4,082,567 | 4/1978 | Conklin et al. | 134/22.11 |
| 5,161,911 | 11/1992 | Regan | 137/236.1 |

Primary Examiner—R. Bruce Breneman
Assistant Examiner—Saeed T. Chaudhry
Attorney, Agent, or Firm—Marger, Johnson, McCollom & Stolowitz

[57] ABSTRACT

A method for collecting and treating small particulate pollutants typically found on the surface of streets in areas where the storm sewer and sanitary sewer are maintained separately. The method includes temporarily isolating a portion of the storm sewer in the immediate vicinity of the street to prevent any collected runoff from passing into the storm sewer, and then flushing the street with a stream of water to remove and collect the solid pollutants from the street surface. The flushing water containing the removed solid pollutants is collected and contained in the isolated storm sewer portion, and is then pumped into the sanitary sewer system for treatment in existing sewage treatment facilities.

3 Claims, 3 Drawing Sheets

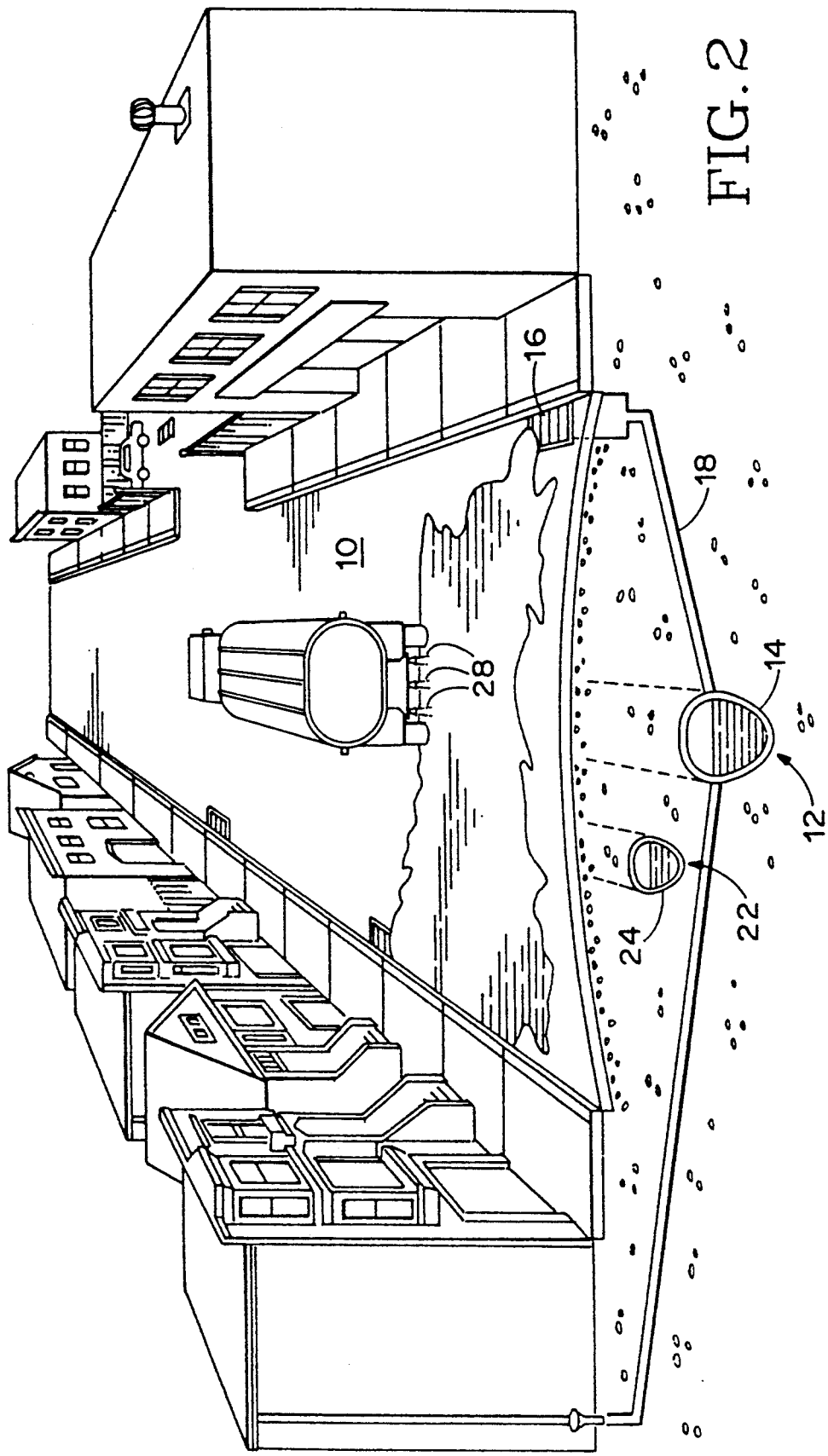

METHOD FOR CONTROLLING STREET SURFACE POLLUTANTS

BACKGROUND

1. Field of the Invention

The present invention relates generally to pollution control, and more specifically to collection and treatment of solid pollutants which collect on the surface of streets.

2. Description of Related Art

Significant efforts and resources are being expended to identify and control various sources and types of pollution. Pollutants emitted from automobiles are among the most notorious and visible, and therefore have been the subject of extensive abatement efforts for more than 25 years. The primary focus in controlling automobile emissions however has been on controlling airborne pollutants such as unburned hydrocarbons, carbon monoxide, $NO_x$, and sulfur containing compounds. Another significant, yet largely unrecognized form of pollution by automobiles occurs in the form of small particulates which collect on the surface of streets. Some of these particulate pollutants originate as solid or liquid combustion products which settle or condense on the street surface. Others are generated by the normal wear of frictional mechanisms such as brakes and clutches, or by the normal wear of tires and auxiliary drive belts fitted to most automobiles.

These particulate pollutants as a group contain numerous substances, some of which may be water-soluble, which are problematic if allowed to accumulate, including polynuclear aromatic hydrocarbons, oils, greases, rubber particles, solid carbonaceous combustion products, and metals such as copper, lead and zinc. If left to accumulate on the street surface, some of these pollutants are continually disturbed by vehicles using the streets and circulated in the form of airborne dust. If left to be finally carried off by the natural action of rain, the pollutants may end up on local bodies of water, which may themselves be the subject of extensive anti-pollution efforts.

The problem can be particularly acute in areas which experienced periods of little or no rainfall. The shortage of rainfall impacts this problem in more ways than one. First, if there is an extended period without rainfall, the pollutants will continue to accumulate on the street surfaces during that period. Secondly, it is often during these times of low rainfall that local bodies of water experience low flows, or reduced volumes. When rain does finally fall, a relatively large amount of solid pollutants which have been accumulated are then suddenly discharged into a relatively low volume of water, resulting in relatively high pollutant concentrations.

Up until now there has been very little effort devoted to control of these solid street surface pollutants, and no satisfactory solution to their removal and control has been found. Normal street sweeping is used to remove debris and larger particles. Sweepers may be equipped with vacuum cleaning equipment, but such equipment has not been shown to be effective at removing small particulate pollutants from the surface of the street. As a result, these pollutants normally end up being discharged untreated with storm water runoff. This is particularly true in areas where the storm sewer system is separate from the sanitary sewer system. In these instances, pollution treatment facilities are normally provided only on the sanitary sewer system, with no provision made for treatment of the storm sewer discharge. There is minimal treatment of collected street surface runoff in some cases, but mostly in the form of swirl concentrators or similar devices. Swirl concentrators typically remove 10-30% of the suspended solids, but are ineffective at removing extremely small particles and dissolved pollutants.

Efforts at education raise awareness of the problem, and may serve to reduce vehicle usage overall, but have no effect on controlling whatever quantity of pollutants which find their way to the street surface.

A need therefore remains for a method of collecting and treating small particulate pollutants from street surfaces which otherwise go untreated.

SUMMARY OF THE INVENTION

The present invention comprises a method for collecting and treating the small particulate pollutants typically found on the surface of streets in areas where the storm sewer and sanitary sewer are maintained separately. The method generally comprises temporarily isolating a portion of the storm sewer in the immediate vicinity of the street to prevent any collected runoff from passing into the storm sewer, and then flushing the street with a stream of water to remove and collect the solid pollutants from the street surface. The flushing water containing the removed solid pollutants is collected and contained in the isolated stonu sewer portion, and is then pumped into the sanitary sewer system. The collected flushing water and solid pollutants are then carried by the sanitary sewer, together with the sanitary sewerage, to existing treatment facilities for separation of the pollutants from the flushing water by known methods.

The present invention also comprises isolating the local portion of the storm sewer by use of an inflatable bladder which, when inflated, sealingly engages the inner walls of the storm sewer, and contains the flushing water until it is pumped into the sanitary sewer system.

BRIEF DESCRIPTION OF THE FIGURES

FIG. 2 is a perspective view of a street being flushed to collect solid pollutants from its surface.

DETAILED DESCRIPTION OF THE PREFERRED EMBODIMENT

Figure 1:
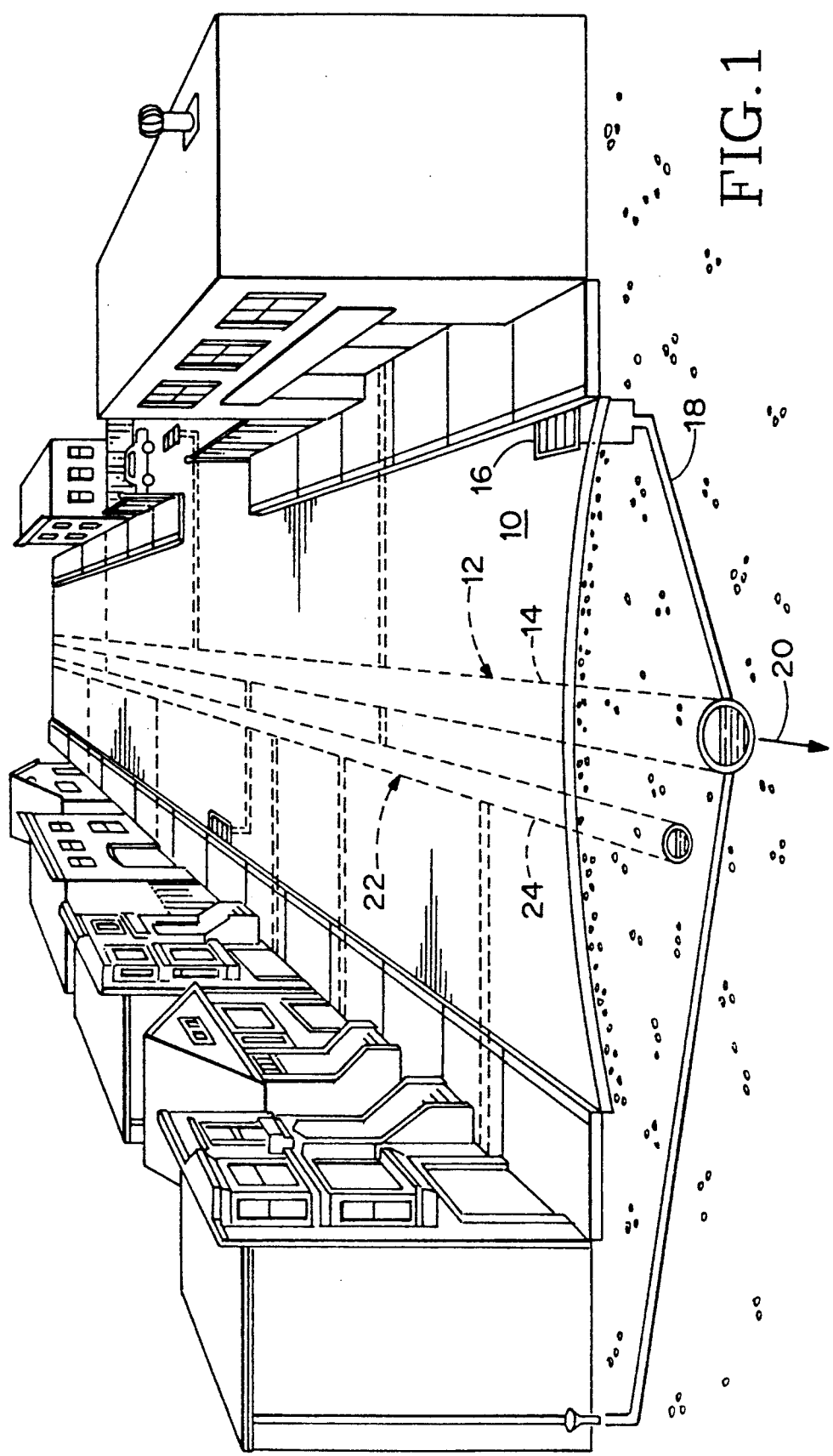
FIG. 1 is a perspective view of a typical street showing separate sanitary and storm sewer systems.

Referring now to FIGS. 1 and 2, a street surface to be cleaned is shown generally at 10. A portion of a storm sewer system is shown at 12, and includes collector pipe 14 for receiving runoff which enters the system through opening 16 and branch line 18. Runoff collected in collector pipe 14 continues to flow downstream in the direction of arrow 20 to a remote discharge point (not shown). A separate sanitary sewer system 22 includes main pipe 24, and a manhole 30 (FIG. 2) which allows for the introduction of additional waste into sanitary sewer system 22 when required.

Figures 3, 4:
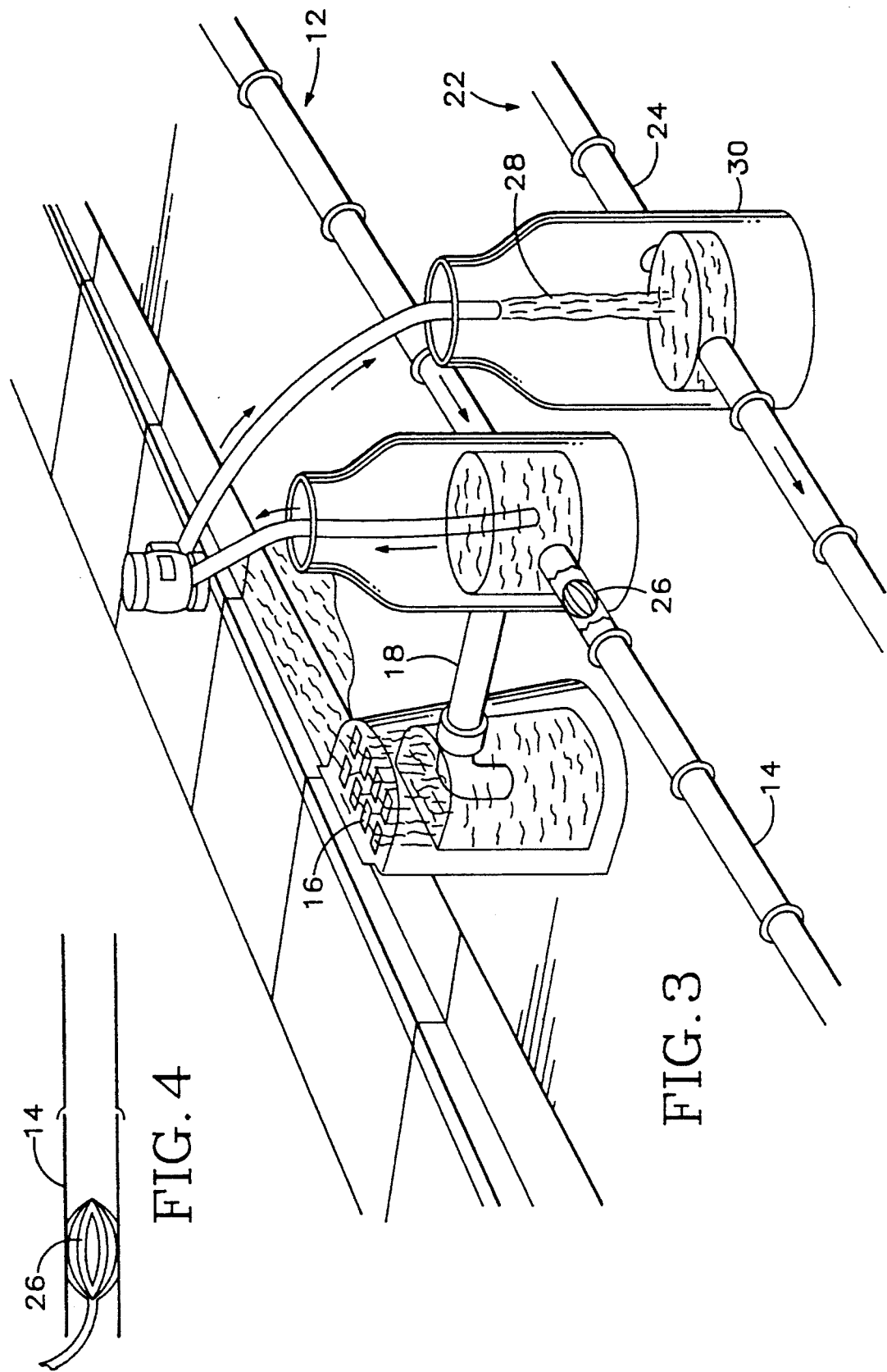
FIG. 3 is a side schematic view of a storm sewer system showing the location of the inflated sealing bladder for isolating a portion of the storm sewer for collecting the flushing water and collected pollutants.
FIG. 4 is a cross-sectional view of the inflated bladder in place in the storm sewer collector pipe.

Referring to FIGS. 3 and 4, in preparation for removing and collecting pollutants from the street surface 10, bladder 26 is inserted into collector pipe 14 of storm sewer system 12 and inflated to seal off collector pipe 14 from the downstream portion of storm sewer system 12. Bladder 26 is preferably a peterson 12" Inflatable Stopper, Model 12-4120 available from Peterson Product Company of Fredonia, Wis. Those skilled in the art will recognize that other suitable methods may be used to seal off the stonu sewer. Bladder 26 is inflated sufficiently to engage the walls of collector pipe 14 with sufficient force to form a substantially watertight seal between bladder 26 and collector pipe 14. Street surface 10 is then flushed by conventional means with one or more streams of flushing water 28 to dislodge and dissolve solid pollutants (not shown) thereon. In some cases reclaimed treated waste water may be used for flushing. Preferably, street surface 10 may be pre-wetted with a detergent solution prior to flushing to facilitate a more thorough pollutant removal, although this step is not required. Solid pollutants are dissolved or entrained in the flushing water 28, which flows down the slope of the crowned street surface 10 toward grate 16. Flushing water 28 enters grate 16, and flows through branch line 18 into collector pipe 14, where it accumulates in collector pipe 14 upstream of bladder 26. Preferably during the collection and accumulation of flushing water 28 in collector pipe 14, flushing water 28 is simultaneously being pumped out of collector pipe 14 into manhole 30 of sanitary sewer system for delivery, together with the sanitary sewerage, to a treatment facility to remove the collected pollutants from flushing water 28. During dry weather, treatment facilities normally achieve a high level of pollutant removal from the accumulated waste waters conveyed to them (e.g., greater than 85%). The collected flushing water will thus receive a similar degree of treatment which is much superior to the generally non-existent treatment received by storm water flows in separated sewer systems. After being treated, flushing water 28 may then be discharged, or possibly reused for further flushing of streets.

While the present invention has been described by means of the preferred embodiment, those skilled in the art will recognize that numerous modifications in detail are possible without departing from the scope of the claims. I hereby claim all such modifications.

I claim:

1. A method for collecting and treating pollutants from the surface of a street comprising the steps of:
   a. providing a sanitary sewer system for collecting, diverting and treating sanitary wastes;
   b. providing a storm sewer system, said storm sewer system including a first portion for collecting surface water runoff from said street surface, and a second portion communicating with said first storm sewer portion, said storm sewer second portion for receiving and diverting said surface water runoff from said first storm sewer portion to a remote location, said storm sewer system isolating said surface water runoff from said sanitary sewer system;
   c. temporarily sealingly isolating said second storm sewer portion from said first storm sewer portion;
   d. flushing the surface of said street with flushing water to collect and remove surface pollutants therefrom;
   e. collecting said flushing water and surface pollutants in said storm sewer first portion; and
   f. transferring said flushing water and surface pollutants from said storm sewer first portion to said sanitary sewer; and
   g. treating said collected surface pollutants in said sanitary sewer system.

2. The method of claim I wherein said step of temporarily sealingly isolating said second storm sewer portion from said first storm sewer portion comprises the steps of:
   a. providing an inflatable bladder
   b. placing said inflatable bladder in said storm sewer first portion at a preselected location in said storm sewer first portion ; and
   c. inflating said inflatable bladder to sealingly engage the walls of said storm sewer first portion, thereby temporarily sealingly isolating said storm sewer second portion from said storm sewer first portion.

3. The method of claim 1 which further comprises applying a detergent to said street surface prior to flushing said street surface.

* * * * *